United States Patent
Schiene et al.

(10) Patent No.: US 8,834,789 B2
(45) Date of Patent: Sep. 16, 2014

(54) FLUID TREATMENT SYSTEM COMPRISING RADIATION SOURCE MODULE AND COOLING MEANS

(75) Inventors: Wolfgang Schiene, Wuerselen (DE); Georg Greuel, Roetgen (DE)

(73) Assignee: Koninklijke Philips N.V., Eindhoven (NL)

( * ) Notice: Subject to any disclaimer, the term of this patent is extended or adjusted under 35 U.S.C. 154(b) by 1025 days.

(21) Appl. No.: 12/307,946

(22) PCT Filed: Jul. 5, 2007

(86) PCT No.: PCT/IB2007/052640
§ 371 (c)(1),
(2), (4) Date: Jan. 8, 2009

(87) PCT Pub. No.: WO2008/010132
PCT Pub. Date: Jan. 24, 2008

(65) Prior Publication Data
US 2009/0257926 A1 Oct. 15, 2009

(30) Foreign Application Priority Data
Jul. 13, 2006 (EP) .................................... 06117090

(51) Int. Cl.
*A61L 2/10* (2006.01)
*C02F 1/32* (2006.01)

(52) U.S. Cl.
CPC .... *C02F 1/32* (2013.01); *A61L 2/10* (2013.01)
USPC ............................................... 422/24; 422/22

(58) Field of Classification Search
CPC ..................................... A61L 2/10; A61L 2/08
USPC ......................................................... 422/24, 22
See application file for complete search history.

(56) References Cited

U.S. PATENT DOCUMENTS

| | | | |
|---|---|---|---|
| 4,693,870 A | 9/1987 | Gloor et al. | |
| 4,837,484 A | 6/1989 | Eliasson et al. | |
| 5,136,170 A | 8/1992 | Gellert | |
| 5,194,740 A | 3/1993 | Kogelschatz et al. | |
| 5,834,784 A | 11/1998 | Morgan et al. | |
| 6,177,763 B1 | 1/2001 | Morrow | |
| 6,201,355 B1 | 3/2001 | Morgan et al. | |
| 6,633,109 B2 | 10/2003 | Falkenstein | |
| 7,683,343 B2 * | 3/2010 | Schiene et al. | 250/432 R |

FOREIGN PATENT DOCUMENTS

| | | |
|---|---|---|
| JP | 06210286 A | 8/1994 |
| JP | 07288112 A | 10/1995 |
| JP | 2005313174 A | 11/2005 |

* cited by examiner

*Primary Examiner* — Lyle Alexander

(57) ABSTRACT

In a fluid treatment system includes a housing with fluid inlet and outlet for a process fluid, an irradiation zone disposed between the fluid inlet and fluid outlet, and at least one radiation source module with a radiation source having a discharge vessel with outer and inner wall. The inner wall encloses an internal volume with at least one opening and an internal electrode for igniting and maintaining a discharge. The radiation source module also includes a submersible frame with a guide to guide the process fluid into and out of the internal volume of the radiation source. The dissipation of the heat generated by the discharge in the discharge gap via a fluid flow in the internal volume of the lamp and in contact with the internal electrode is substantially more effective than dissipation via a cooling channel separated from the internal electrode. It is therefore substantially easier to maintain the discharge at an approximately optimal temperature.

18 Claims, 1 Drawing Sheet

FLUID TREATMENT SYSTEM COMPRISING RADIATION SOURCE MODULE AND COOLING MEANS

FIELD OF THE INVENTION

Figure 1:
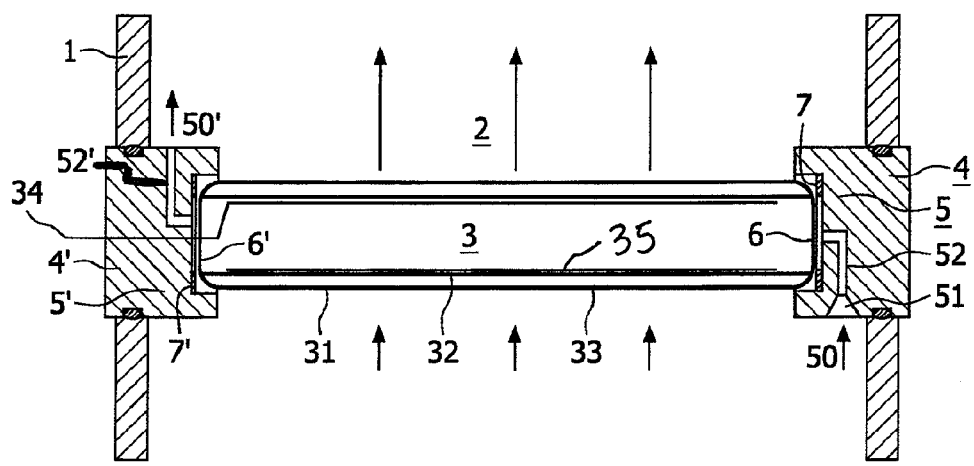

The invention relates to a fluid treatment system for treating a fluid by exposing it to high-energy radiation. The fluid treatment system comprises a housing for receiving a flow of fluid with a fluid inlet, a fluid outlet, an irradiation zone disposed between the fluid inlet and the fluid outlet, and at least one radiation source module disposed in the irradiation zone. The at least one radiation source module comprises at least one high-energy radiation sources and cooling means for said high-energy radiation source.

As a radiation source a dielectric barrier discharge lamp is especially contemplated.

BACKGROUND OF THE INVENTION

For fluid treatment systems using exposition to high-energy radiation, especially high-energy ultraviolet radiation, there are various applications such as, for example, sterilization, curing of lacquers and synthetic resins, flue-gas purification, destruction and synthesis of special chemical compounds.

Further applications for the device according to the invention have to do with water and wastewater technology where polluted water is the fluid to be treated. Examples of treatment of this kind that may be mentioned are a) disinfection b) breakdown of pollutants and dyes and removal of odor and c) destroying solvent residues present in water.

The device according to the invention may also be used for the treatment of other liquids and solvents besides water, as well as for the treatment of gases.

These applications are generally based on photo-physical or photochemical processes. For use in any of these processes, the radiation source must be able to effectively irradiate the process fluid with high-energy radiation, such as (V) UV radiation, since it is the (V) UV photon that starts the desired photo-physical or photochemical reaction. Also, the wavelength of the radiation should be tuned very precisely to the intended process.

Therefore, fluid treatment by photophysical or photochemical processes requires radiation sources that provide high intensity UV radiation, preferably UV radiation, emitting specific radiation in a narrow wavelength range.

These requirements are excellently met by excimer lamps, provided among other things in the form of dielectric barrier discharge (DBD) lamps. In DBD lamps, the electrical energy is coupled by capacitive means to the discharge volume. A DBD lamp can be realized when a high voltage is applied across a gas-filled discharge gap, which is separated from electrodes by at least one dielectric barrier. Dielectric barriers include, for instance, glass or quartz. Due to the nature of the discharge to generate non-thermal plasmas at atmospheric gas pressure, excited diatomic molecules (excimers) are produced, when rare gases, or mixtures of rare gases and halogens are used as the discharge gas. The excimers emit high-energy radiation in the ultraviolet spectral range when they decay.

A dielectric barrier discharge lamp has various advantages which neither a conventional mercury low-pressure lamp nor a conventional high-pressure arc discharge lamp have; for example, emission of ultraviolet radiation with short waves, such as 172 nm, 222 nm, and 308 nm, and at the same time generation of light with individual high-efficiency wavelengths which are roughly like line spectra, are achieved. The emission wavelength depends on the type of gas filling, e.g. xenon filling provides emission at 172 nm.

For fluid treatment systems typically a dielectric barrier discharge lamp of the double tube type is used, which consists of an inner tube and an outer tube.

That is to say, the wall of the inner tube spans a cavity, which likewise forms a type of turned-in section in the discharge vessel, in which one or more internal electrodes are located.

For safety, the internal electrode is located on the high-voltage side and the electrode located in the outer tube is located on the grounded side. In this manner, the internal electrodes are protected against unintentional access.

There is a tendency to use the minimum number of lamps possible and run them at high power density.

As a lamp run at a high power density has a higher internal temperature than a lamp run at a lower power, there is the problem that during use the electrodes and discharge gas can be overheated. Overheating the electrodes alters the wavelength of the emitted radiation, reduces the lamp efficiency and can lead to degradation of the electrodes and the dielectric material, reducing the useful lifetime of the lamp.

As a result of temperature differences within the discharge vessel, there may also be differences in the wavelengths of the emitted radiation generated by the lamp. This results in a broader spectrum of emitted radiation, which can have undesired consequences on fluid treatment processing.

Thus, a significant problem in the art is how to overcome these differences in temperatures locally within the devices, and how to keep the lamp cool enough to efficiently generate UV or VUV radiation.

From U.S. Pat. No. 5,834,784 a lamp is known that is constructed in the form of two concentric quartz cylinders sealed together at their ends with the excimer gas fill between the cylinders. Cooling liquid is pumped through the central region inside the inner quartz cylinder where an electrically conductive pipe which is not in contact with the inner cylinder is used to supply this cooling liquid. Although it is not in contact with the inner quartz cylinder, this central pipe also acts as the high-voltage electrode. A cable attaches the central pipe to a high-voltage AC power source, but this high-voltage electrode is electrically insulated from the source of cooling liquid by a suitably long length of electrically insulated tubing which also supplies the cooling liquid.

Under the rough conditions in a water treatment plant, such lamp may provide a safety hazard, if the electrically insulated tubing is not carefully protected against unintended breakage.

Thus the principal object of the present invention is to create an internal cooling for a radiation source according to the prior art, which does not impair the operational safety of the fluid treatment system, but which nevertheless makes possible an efficient cooling of the inner tube of the radiation source.

SUMMARY OF THE INVENTION

To address these problems, this invention provides a fluid treatment system comprising a housing with a fluid inlet and a fluid outlet for a process fluid, an irradiation zone disposed between the fluid inlet and fluid outlet, and at least one radiation source module comprising at least one radiation source comprising a discharge vessel with an outer wall and an inner wall, the inner wall enclosing an internal volume with at least one opening and means for igniting and maintaining a discharge, the radiation source module also comprising a submersible frame with guiding means to guide the process fluid into and out of the internal volume of the radiation source.

During operation the process fluid is passed through the internal volume of the radiation source and acts as a coolant.

The essential advantage of the invention is to be seen in the fact that the dissipation of the heat generated by the discharge in the discharge gap via a fluid flow in the internal volume of the lamp and in contact with the internal electrodes is substantially more effective than dissipation via a cooling channel separated from the internal electrode. It is therefore substantially easier to maintain the discharge gas at an approximately optimal temperature. At the same time, strong cooling is provided at no extra cost.

Both improvements allow this UV source to be used for high-powered application in water treatment.

According to a preferred embodiment of the invention, the radiation source is a dielectric barrier discharge lamp. Such lamps have narrow spectra in the desired wavelength ranges, have a narrow distribution of intensity of the emitted radiation and are convenient and relatively inexpensive to manufacture and operate.

According to the invention the guiding means to guide the process fluid into and out of the internal volume of the radiation source comprise at least one terminating end cap that tightens the at least one opening of the internal volume of the radiation source and comprises an inlet port and an outlet port for the process fluid.

According to a preferred embodiment of the invention the internal volume of the radiation source comprises a first opening and a second opening, terminated by a first end cap and a second end cap, wherein the first end cap comprises an inlet port and the second end cap comprises an outlet port.

According to another preferred embodiment the guiding means comprise baffling means.

The frame may also comprise means to enhance the flow of the process fluid trough the internal volume of the radiation source. This increases the velocity of the first fluid and improves heat transfer.

Preferably, the means for igniting and maintaining a discharge comprise at least one first low-voltage, grounded electrode attached to the outer wall of the discharge vessel and at least one second high-voltage electrode attached to the inner wall of the discharge vessel.

According to a preferred embodiment the first electrode of the radiation source is comprised of the process fluid, the process fluid being electrically conductive.

If the process fluid is adjacent to and in thermal contact with the outer wall of the radiation source discharge gap, it serves to carry excess heat away from the discharge vessel.

DETAILED DESCRIPTION OF THE INVENTION

The present invention provides a fluid treatment system comprising a housing for receiving a flow of fluid, the housing comprising a fluid inlet, a fluid outlet, an irradiation zone disposed between the fluid inlet and the fluid outlet, and at least one radiation source module comprising a radiation source to irradiate the fluid.

As is known to those of skill in the art, the dosage of radiation received by the fluid is the product of the radiation intensity and the exposure time. The intensity of the radiation varies with the square of the distance the radiation passes through, but the exposure time varies linearly with the fluid flow velocity. Accordingly, it is desired to maintain the fluid to be treated as close as possible to the radiation sources.

To this aim, the at least one radiation source module includes at least one radiation source mounted within a submersible frame. During operation the frame enclosing the radiation source is immersed into the fluid to be treated, which is then irradiated as required.

Conventional systems often incorporate more than one, i.e. an array of radiation sources attached to a common frame.

The radiation source is selected from but not limited to low or medium pressure mercury lamps, pulsed Xenon and mercury discharge lamps, and dielectric barrier discharge lamps.

Preferably a dielectric barrier discharge lamp is used as the radiation source. A dielectric barrier discharge (DBD) lamp for generating and emitting an ultraviolet radiation comprises a discharge gap being at least partly formed and/or surrounded by at least an inner wall and an outer wall, whereby at least one of the walls is a dielectric wall and at least one of the walls has an at least partly transparent part. The outer wall and the inner wall are laterally sealed to each other so as to form the discharge vessel.

In lamps useful for the present invention the inner wall of the discharge vessel surrounds an internal volume. Vice versa, the internal volume is surrounded by an annular-shaped discharge vessel. Otherwise the geometry of the radiation source can be adapted within wide limits to the process in which it is employed. Preferably, the lamp geometry is selected from the group comprising to large-area flat box-shaped lamp geometry, coaxial lamp geometry, dome-shaped lamp geometry, and the like.

Radiation sources especially useful for the invention are elongated and have a longitudinal axis substantially perpendicular or parallel to the direction of fluid flow through the irradiation zone and are fully submersed in the fluid flow through the irradiation zone. Accordingly, the internal volume of the lamp is an elongated space with a longitudinal axis perpendicular or parallel to the direction of the fluid flow.

For industrial purposes coaxial DBD-lamps with relatively large diameters of the internal volume compared to the diameter of the discharge gap are preferred to achieve a lamp that is easy to produce and comprises a large effective area and a high mechanical stability.

For coaxial lamps, the discharge vessel is generally cylindrical and comprises an inner tube wall and an outer tube wall coaxially disposed about the center axis of the annular shaped discharge vessel sealed together at the ends with the gas fill between the inner and outer tube. The internal volume comprises two laterally displaced open endings.

For dome-shaped lamps, the discharge vessel is generally cylindrical and comprises an inner tube wall and an outer tube wall coaxially disposed about the center axis of the discharge vessel and the inner tube as well as the outer tube are closed laterally by a calotte, a plate or the like. The internal volume comprises one closed end and one opening at the distal end of the internal volume.

The material for the dielectric walls is selected from the group of dielectric materials. Also the material for the dielectric walls have to be selected such that the radiation generated inside the discharge gap can pass via at least part of the outer dielectric wall for applying the radiation for the fluid treatment. Quartz glass is a preferred dielectric material.

The dielectric walls of the lamp can be additionally covered or coated on their inner or outer surfaces with a phosphor or a luminescent layer for converting/shifting the spectrum of the radiation generated inside the discharge gap towards higher wavelengths.

The annular-shaped discharge space of the discharge tube is filled with a discharge gas to create excimer molecules as a result of dielectric barrier discharge.

The discharge gas typically comprises an inert gas or a substance forming excimers under discharge conditions for example, a noble gas, a or a noble gas/metal vapor mixture, noble gas/halogen mixture, if necessary using an additional further noble gas (Ar, He, Ne) as a buffer gas.

The wavelength of the radiation varies by the kind of the discharge gas and type of luminescent coating and may range, for example, in the UV, (V) UV, Infrared, visible light, or any other applicable range.

The dielectric discharge necessary to form the radiating excimer species is generated when an electrical field is created between electrodes with high resistance to electric current flow between them.

Therefore the means to ignite and maintain a discharge of the radiation source comprise at least one first low-voltage grounded electrode and at least one second high-voltage electrode that are separated by a dielectric barrier from the discharge gap to provide the large resistance to the flow of electrical current between the electrodes and which have a high capacitance.

For safety, the high-voltage electrode is attached to the inner wall of the discharge vessel and the low-voltage electrode is attached to the outer wall and is grounded. The reason for this is that there is only a small probability that the inside high-voltage electrode will come into contact with individuals and the like.

The internal electrode may have an optically opaque characteristic in order to prevent the high-energy radiation emitted from the discharge to enter the internal volume of the lamp.

The shape of the internal electrode is preferably a shape, which is in close contact with the surface of the inner wall. So the internal electrode can be formed by a method in which the internal electrode is directly formed on an inner face of the inner tube by metal coating, or a method in which a metal plate having a shape in agreement with the shape of the inner face of the inner tube is inserted, or other methods.

Suitable materials for use for the internal electrodes are corrosion-resistant materials, such as silver, gold, platinum, stainless steel, aluminum, aluminum alloy, copper, copper oxide, alloy containing copper, alloy containing copper oxide or the like.

The shape of the external electrode is also preferably a shape that is in close contact with the outer surface of the discharge vessel.

It is important that the radiation can emerge through the external electrode. This problem can be solved with optically transparent, electrically conducting layers or else by using a fine-mesh wire grid, perforated plate or deposited linear strips as an electrode, which are substantially transparent to the radiation.

As the external electrode, it is preferable to use a corrosion-resistant material made of silver, gold, platinum, stainless steel, aluminum or the like.

In the fluid treatment system according to the invention the process fluid is in direct contact with the outer surface of the DBD lamp. If the process fluid is a good conductor of electricity, it can be used as a low-voltage grounded electrode for the DBD lamp.

So according to one preferred embodiment of the invention the irradiated fluid is directly used as a low-voltage and grounded external electrode instead of a metallic external electrode.

Alternatively, the second high-voltage electrode may be comprised of the process fluid, if the process fluid is electrically conductive.

This is advantageous, since in this manner the radiation generated penetrates directly into the fluid to be irradiated and the fluid simultaneously serves as a coolant.

Also the absence of the metallic mesh external electrode increases the amount of emitted radiation, since no radiation is lost due to absorption/reflection by the metallic mesh.

Besides electrodes the means for igniting and maintaining a discharge also comprise electrically conduit members adapted to connect the pair of electrodes to a high-voltage high-frequency power source for applying a high voltage between the pair of electrodes and generating an electric discharge between the electrode surfaces. Such devices are well known in the art and will not be described further.

A dielectric barrier discharge lamp generates heat upon radiation. In order to prevent the discharge vessel and the electrodes from being overheated, according to the invention the process fluid is arranged to flow through the internal volume of the lamp to provide additional cooling.

To this aim the radiation source module is comprised in a submersible frame comprising guiding means to guide the process fluid into and out of the internal volume of the radiation source for cooling the internal electrode.

Preferably, the frame is secured to the housing by support members. The support members may be attached anywhere below the level of fluid in treatment system and it may be possible to detach the lamp.

According to a preferred embodiment, the shape of the radiation source is an elongated tube with a longitudinal axis and said frame comprises support members to keep the longitudinal axis of the radiation source in a position substantially perpendicular to the flow of the process fluid.

The frame also comprises at least one terminating end cap to separate the at least one opening of internal volume of the lamp from the process fluid. Typically the terminating end cap is integrated in a support member.

The at least one end cap is provided so as to seal hermetically the at least one opening of the internal volume of the lamp from the housing to prevent direct contacting of the internal volume and the fluid flow in the housing to avoid an alternative pathway for electrical energy to flow away from the discharge gap and a leakage of current to electrical grounds.

The frame also comprises a feedthrough for the conduit means that connect the internal electrode to the source of high-frequency, high-voltage excitation voltage, which is secured with respect to the end cap and the housing by means of an insulating collar.

The opposite end of the radiation source is also attached to a support member, which is in turn attached to the housing. Where the lamp design comprises a second opening at the opposite end, this opening is also secured in and end cap integrated in the support member.

The frame also comprises an inlet port for the introduction of process fluid to the internal volume of the lamp and an outlet port for the exhaustion of the process fluid from the internal volume of the lamp.

The inlet port, the internal volume of the lamp and the outlet port are connected to define a fluid flow passage way over essentially the whole width of the lamp.

It will be appreciated that the design of the inlet and outlet port may vary depending on the configuration of the fluid flow passage.

According to one embodiment of the invention the frame comprises at least one terminating cap that comprises an inlet port, and/or an outlet port for the process fluid.

One or both of the inlet port and the outlet port may comprise a tapered section perpendicular to the fluid flow direction through the housing. Alternatively, a funnel or bell-mouth shaped inlet and outlet may be utilized.

The inlet communicates with the internal volume of the lamp through a bore, which is in the form of a manifold formed in the end cap. The inlet manifold is illustrated in the drawings as an arcuate bend of rectangular cross section.

The outlet port communicates with the interior of the lamp through a similarly shaped outlet manifold. Although manifolds are shown to be of rectangular shape, it will be appreciated that the manifolds may be of any suitable cross-sectional shape, for example circular.

It should be noted that the high-voltage internal electrode and the grounded electrode are electrically connected via the cooling channel fluid flow passageway through the internal volume of the lamp.

For potential isolation between the high-voltage electrode and the grounded electrode the fluid flow passage has to be designed as a long path having sufficiently high electrical resistance to minimize the likelihood that the coolant would be a alternative pathway for electrical current flow between internal and external electrodes.

By making the passageway thin and as long as possible, the lateral resistance between the electrodes over the coolant channel is higher than the sum of the impedances of the dielectric layers above the electrodes and the discharge gas in the discharge space. Thus the preferred current flow takes place from one electrode through the dielectric layer through the gas and through the other part of the electrode rather than between the electrodes directly via the fluid passage pathway dielectric layer of the second electrode.

To make the passageway a long as possible the bores might be designed as multiple arcuated bends or helices.

In one embodiment of the invention the internal volume of the radiation source comprises a first opening and a second opening, terminated by a first end cap and a second end cap, wherein the first cap comprises an inlet port and the second cap comprises an outlet port in fluid communication with the axial passageway through the internal volume of the lamp, the first inlet and the first outlet being axially spaced apart.

In this configuration the flow of the process fluid is parallel to the internal electrode and is therefore perpendicular to the discharge gap.

As a result, the inner wall of the discharge vessel and the internal electrode can be cooled sufficiently because the guiding means accommodate a flow of process fluid in an axial direction parallel to the internal electrodes through the internal volume of the lamp.

For particularly long separation between the internal and the external electrodes, baffling means may be employed in the fluid passage way for causing the fluid to travel along a fluid passage way on a path having axial and/or radial components, e.g. on a meander, spiral or sinusoidal path. The baffling means also act as turbulizers to enhance heat exchange.

Baffling means may preferably comprise axial or radial fins as flow guides, causing the fluid to make a number of axial or radial turns as it flows between the inlet and the outlet port.

Figure 2:
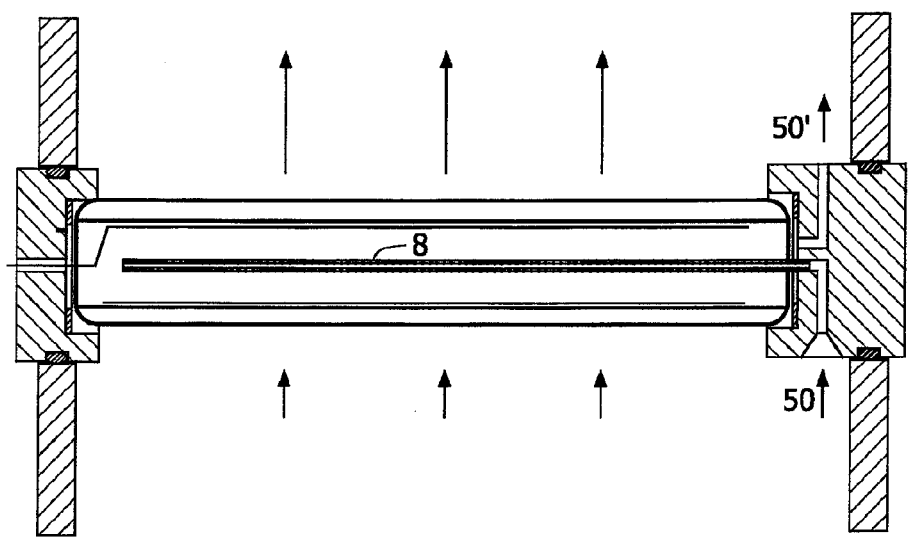

In one exemplary embodiment of the invention shown in FIG. 2, an axial fin is provided as a reduced diameter hollow tube, whose external diameter is less than the inner wall of the lamp, extends along only part of the length of the inner wall of the lamp and leaves an annular gap between itself and the inside wall.

The provisions of the baffling means ensures that the at least one end of the axial fin is in a sealed communication with the inlet and/or outlet port, thereby ensuring an efficient extension of the axial flow passageways.

In the exemplary embodiment according to FIG. 2 the reduced-diameter hollow pipe extends into bore of an inlet or outlet port of the end caps and thereby communicates with the fluid flow in the housing.

Therefore, an axial fluid flow passageway is formed between the inlet port and the outlet port to accommodate flow of process fluid in alternating directions parallel to the internal electrodes through the internal volume of the lamp. This increases the length of the fluid passage way and improves heat transfer.

In the exemplary embodiment according to FIG. 2, inflow and drainage of the process fluid via baffling means takes place at one and the same end of the internal volume of the lamp. It is of course within the scope of the invention to provide the flow passageway with more than one co-axial or parallel hollow pipes as the baffling means, which are mutually offset relative to alternating distal end caps.

Although the preferred pipes shown and described herein comprise cylindrical pipes, it will be appreciated that the pipes may be of other suitable shapes. For example, the pipe may have the same or a different cross-sectional shape selected from rounded shapes and multi-sided shapes. Preferred rounded shapes include circular, oval, elliptical, etc. and preferred multi-sided shapes include regular or irregular polygons such as square, rectangular, pentagonal, hexagonal, etc. The annular spaces between the pipes and the inner wall of the discharge vessel would of course take on shapes, which are dictated by the shapes of the pipes and the inner wall.

Another alternative is to provide each end cap with an inlet port and an outlet port and appropriate baffling means within the internal volume of the lamp for two axial flow passages for opposite flow directions.

In an embodiment according to this alternative of the invention the hollow pipe extends axially along the entire length of the internal volume of the lamp and is secured to an inlet port of a first end cap and an outlet port of the distal end cap.

Then a first axial fluid flow passage way is defined from the inlet port of the first end cap to the outlet port of the second end cap through the reduced-diameter hollow pipe. By this the contact of the process fluid with the internal electrode is avoided.

Also an axial second fluid flow is defined in the opposite direction from the inlet port of the second end cap to the outlet port of the first end cap through the annular gap between the reduced-diameter hollow pipe and the inner wall of the lamp.

In still another embodiment of the invention the cooling channel may comprise baffling means to accommodate flow of process fluid in directions perpendicular to the internal electrodes through the internal volume of the lamp to further enlarge the distance. Such baffling means may comprise a single coiled or multiple coiled hollow pipe or a pipe bent into the form of a hairpin Besides means to guide the process fluid through the internal volume of the lamp, the cooling means may also comprise means to enhance the circulation of the process fluid through the internal volume of the lamp.

The source of enhanced circulation of the flow of fluid through the internal volume of the lamp is not particularly restricted. For example, the circulation can be generated by either the hydrostatic pressure, or the hydraulic flow pressure, or the barometric pressure of the process fluid. Hydrostatic and hydraulic pressure can be modified locally—at the entry and/or exit port—to enhance the cooling flow. For example a local increase of the velocity of the process water close to the entry port to the inner cooling will increase the hydraulic (flow) pressure on the port, thus channeling a large flow of cooling fluid through the inner part of the lamp.

As an alternative, the cooling flow can be sustained by hydraulically or pneumatically or electrically driven pumps, located inside the housing used to treat the process fluid. By preference, a hydraulically driven pump is used. The energy required to drive the pump is extracted from the process fluid, without the need of having any additional connection to the outside of the container. With properly shaped DBD lamps and suitable pumps geometries, these elements can also be included in the internal volume of lamp.

Specific Embodiments of the Invention

FIG. 1 shows a cross-section of a fluid treatment system according to the present invention. The fluid to be irradiated is fed into a housing 1 comprising a fluid inlet, a fluid outlet, a fluid treatment zone 2 being disposed between the fluid inlet and the fluid outlet, the fluid treatment zone having a DBD lamp as the radiation source 3 disposed therein.

The DBD lamp 3 comprises a double-walled quartz tube 31, consisting of an internal wall 32 and the external wall 33 and containing a filling gas 34. The annular-shaped space between the internal and external walls 32,33 forms the discharge gap.

The DBD lamp 3 is submersed into the process fluid, which serves as a first external low-voltage grounded electrode. The second, high-voltage electrode 35 is constructed as a metal layer on the internal wall 32 of the lamp. An alternating current source, not shown, is connected to these two electrodes.

The DBD 3 lamp is secured to the housing by support members 4, 4' with integrated end caps 5, 5'. End caps 5,5' are tightened to the first and the second opening 6, 6' of the internal volume of the lamp by washers 7,7'. By these washers the internal volume of the radiation source and the internal electrode is hermetically sealed with respect to the fluid in the housing to avoid an alternative passageway of electric current.

End cap 5 is provided with a fluid inlet port 50, which includes an inlet funnel 51 and an elongated bore 52 extending to the first opening of the lamp. End cap 5' is provided with a fluid outlet port 50', which includes an elongated bore 52' extending to the second opening of the lamp.

A fluid passageway is defined by inlet port 50, the internal volume of the lamp and outlet port 50'. The direction of flow of the process fluid is indicated by arrows.

During operation a flow of the fluid is provided from the fluid inlet to the fluid treatment zone in a manner substantially perpendicular to the radiation source; the flow of fluid is irradiated by the DBD lamp in the fluid treatment zone; and the flow of fluid leaves the housing via the fluid outlet. Simultaneously, part of the process fluid is branched off and is conveyed to the internal volume of the lamp and serves simultaneously as a coolant of the internal volume and the internal electrode of the lamp.

Another implementation of a fluid treatment system according to the invention is shown diagrammatically in FIG. 2.

While the general design of the fluid treatment system is the same as in the embodiment according to FIG. 1 in the design according to FIG. 2 end cap 5 is provided with a fluid inlet port 50, which includes an inlet funnel 51 and an elongated bore 52 extending to the first opening of the lamp, as well as with a fluid outlet port 50', which includes an elongated bore 52' extending also to the first opening of the lamp.

Additionally, a reduced diameter hollow pipe 8 is inserted into the internal volume of the lamp and secured to the bore of inlet port 50.

Here the fluid passageway is defined by inlet port 50, reduced-diameter hollow pipe 8, an annular return channel between hollow pipe 8 and the inner wall of the lamp and outlet port 50'.

It should be understood that, while exemplary embodiments of the present invention have been described herein, the present invention is not limited to these exemplary embodiments and that variations and other alternatives may occur to those of skill in the art without departing from the intended scope of the invention as defined by the attached claims.

SHORT DESCRIPTION OF THE DRAWINGS

The drawings show exemplary embodiments of the invention diagrammatically, and in particular.

FIG. 1 shows in section an exemplary embodiment of the invention in the form of a coaxial lamp with means to guide the process fluid through the internal volume of the lamp FIG. 2 shows in section an exemplary embodiment of the invention in the form of a coaxial lamp with baffling means to guide the process fluid through the internal volume of the lamp.

The invention claimed is:

1. A fluid treatment system comprising;
a housing with a fluid inlet and a fluid outlet for a process fluid;
an irradiation zone disposed between the fluid inlet and fluid outlet; and
at least one radiation source module comprising at least one radiation source comprising a discharge vessel with an outer wall and an inner wall, the inner wall enclosing an internal volume with at least one opening and at least one electrode for igniting and maintaining a discharge, the radiation source module also comprising a submersible frame with a cap having an inlet port and an outlet port for guiding the process fluid from an inlet port at a first side of the radiation source into the internal volume of the radiation source for flowing in a first direction towards a second side of the radiation source and for guiding the process fluid to flow in a second direction from the second side to an outlet port at the first side for exit out of the internal volume of the radiation source, wherein the second direction is different from the first direction.

2. The fluid treatment system according to claim 1, wherein the radiation source is a dielectric barrier discharge lamp.

3. The fluid treatment system according to claim 1, wherein the cap tightens the at least one opening.

4. The fluid treatment system according to claim 1, wherein the submersible frame further comprises baffles for the guiding.

5. The fluid treatment system according to claim 1, wherein the frame comprises means to enhance the flow of the process fluid trough the internal volume of the radiation source.

6. The fluid treatment system according to claim 1, wherein the at least one electrode comprises at least one first low-voltage, grounded electrode attached to the outer wall of the discharge vessel and at least one second high-voltage electrode attached to the inner wall of the discharge vessel.

7. The fluid treatment system according to claim 6, wherein the first low-voltage electrode comprises the process fluid, the process fluid being electrically conductive.

8. The fluid treatment system according to claim 6, wherein the second high-voltage electrode comprises the process fluid, the process fluid being electrically conductive.

9. The fluid treatment system of claim 1, wherein the submersible frame further includes a guiding device having a hollow tube in the internal volume for the guiding.

10. The fluid treatment system of claim 9, wherein the hollow tube is configured to receive the process fluid from the inlet port located at the first side and to guide the process fluid in the first direction to the second side for return through the internal volume in the second direction to the outlet port located at the first side, wherein the second direction opposite the first direction.

11. The fluid treatment system of claim 10, wherein the process fluid is electrically conductive and forms a high-voltage electrode.

12. The fluid treatment system of claim 1, wherein the second direction opposite the first direction.

13. The fluid treatment system of claim 9, wherein the guiding device guides the process fluid to flow in the second direction to the outlet port in a channel between an outer wall of the hollow tube and the inner wall enclosing the internal volume.

14. A fluid treatment system comprising;
- a housing with a fluid inlet and a fluid outlet for a process fluid;
- an irradiation zone disposed between the fluid inlet and fluid outlet; and
- at least one radiation source module comprising at least one radiation source comprising a discharge vessel with an outer wall and an inner wall, the inner wall enclosing an internal volume with at least one opening and at least one electrode for igniting and maintaining a discharge, the radiation source module also comprising a submersible frame with a guiding means including a cap having an inlet port and an outlet port for guiding the process fluid from the inlet port at a first side of the radiation source into the internal volume of the radiation source or flowing in a first direction towards a second side of the radiation source and for guiding the process fluid to flow in a second direction from the second side to the outlet port at the first side for exit out of the internal volume of the radiation source, wherein the second direction which is different from the first direction.

15. The fluid treatment system of claim 14, wherein the second direction opposite the first direction.

16. The fluid treatment system of claim 14, wherein the guiding means further includes a hollow tube in the internal volume, wherein the hollow tube receives the process fluid from the inlet port located at the first side and guides the process fluid in the first direction to the second side for return through a channel in the internal volume in the second direction to the outlet port located at the first side, and wherein the channel is between an outer wall of the hollow tube and the inner wall enclosing the internal volume.

17. The fluid treatment system of claim 1, wherein the submersible frame further a includes guiding device includes a hollow tube in the internal volume, wherein the hollow tube extends along only part of a length of an inside wall of the internal volume and leaves a gap between hollow tube and the inside wall, wherein the hollow tube is configured to receive the process fluid from the inlet port located at the first side and to guide the process fluid in the first direction to the second side for exit from the hollow tube into the gap and return through the internal volume in the second direction to the outlet port located at the first side, wherein the second direction opposite the first direction.

18. The fluid treatment system of claim 14, wherein the guiding means further include a hollow tube in the internal volume, wherein the hollow tube extends along only part of a length of an inside wall of the internal volume and leaves a gap between hollow tube and the inside wall, wherein the hollow tube is configured to receive the process fluid from the inlet port located at the first side and to guide the process fluid in the first direction to the second side for exit from the hollow tube into the gap and return through the internal volume in the second direction to the outlet port located at the first side, wherein the second direction opposite the first direction.

* * * * *